(12) United States Patent
Molapo et al.

(10) Patent No.: US 11,670,412 B2
(45) Date of Patent: Jun. 6, 2023

(54) TREATMENT ADHERENCE SYSTEMS AND PROCESSES

(71) Applicant: INTERNATIONAL BUSINESS MACHINES CORPORATION, Armonk, NY (US)

(72) Inventors: Maletsabisa Molapo, Pretoria (ZA); Enas Ahmed Zaki, Ismailia (EG); Vishnupriya Muthukesavaraj, Melbourne (AU); Hyman David Chantz, Scarsdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 283 days.

(21) Appl. No.: 16/880,480

(22) Filed: May 21, 2020

(65) Prior Publication Data

US 2021/0366585 A1 Nov. 25, 2021

(51) Int. Cl.
*G16H 40/67* (2018.01)
*G16H 10/60* (2018.01)
(Continued)

(52) U.S. Cl.
CPC .......... *G16H 30/40* (2018.01); *G06N 20/00* (2019.01); *G06V 10/774* (2022.01); *G06V 10/82* (2022.01); *G06V 40/103* (2022.01); *G16H 10/60* (2018.01); *G16H 20/10* (2018.01); *G16H 30/00* (2018.01); *G16H 40/63* (2018.01); *G16H 40/67* (2018.01); *G16H 80/00* (2018.01)

(58) Field of Classification Search
CPC ........ G16H 20/10; G16H 40/67; G16H 10/60; G16H 30/00; G16H 40/63; G16H 80/00; G06N 20/00; G06V 10/40

USPC ............................................................ 705/2
See application file for complete search history.

(56) References Cited

U.S. PATENT DOCUMENTS 10,037,820 B2 7/2018 Wong et al.
10,231,622 B2 3/2019 Soyao et al.
(Continued)

FOREIGN PATENT DOCUMENTS

WO 2013109864 7/2013

OTHER PUBLICATIONS

Hezarjaribi, N., Fallahzadeh, R., & Ghasemzadeh, H. (Mar. 2016). A machine learning approach for medication adherence monitoring using body-worn sensors. In 2016 Design, Automation & Test in Europe Conference & Exhibition (Date) (pp. 842-845). IEEE. (Year: 2016).*

(Continued)

*Primary Examiner* — Joshua B Blanchette
*Assistant Examiner* — Winston Furtado
(74) *Attorney, Agent, or Firm* — Scott Dobson; Andrew D. Wright; Calderon Safran & Cole, P.C.

(57) ABSTRACT

A method includes: receiving, by a computer device, an association of a prescribed treatment to a user; receiving, by the computer device, an image of the user; receiving, by the computer device, an image of treatment adherence by the user; determining, by the computer device, adherence to the prescribed treatment by analyzing the image of treatment adherence; and generating, by the computer device, a personalized visualization illustrating the determined adherence to the prescribed treatment by modifying the image of the user.

20 Claims, 8 Drawing Sheets

(51) Int. Cl.
*G16H 30/00* (2018.01)
*G16H 20/10* (2018.01)
*G16H 40/63* (2018.01)
*G16H 80/00* (2018.01)
*G06N 20/00* (2019.01)
*G16H 30/40* (2018.01)
*G06V 10/82* (2022.01)
*G06V 10/774* (2022.01)
*G06V 40/10* (2022.01)

(56) References Cited

U.S. PATENT DOCUMENTS

| | | | |
|---|---|---|---|
| 10,303,856 | B2 | 5/2019 | Hanina et al. |
| 2008/0201174 | A1* | 8/2008 | Ramasubramanian ..................... G16H 20/10 705/3 |
| 2015/0363570 | A1* | 12/2015 | Hanina .................... G06K 9/00 348/143 |
| 2017/0140109 | A1* | 5/2017 | Kheifetz ................ G16H 50/20 |
| 2017/0151123 | A1 | 6/2017 | Weffers-Albu et al. |
| 2019/0034581 | A1* | 1/2019 | Aliper ..................... G16B 40/20 |
| 2019/0251723 | A1* | 8/2019 | Coppersmith, III .... G06T 11/60 |
| 2020/0043589 | A1* | 2/2020 | Gyory .................... G16H 20/17 |
| 2021/0027897 | A1* | 1/2021 | Rasochova .......... A61B 5/0013 |
| 2021/0241873 | A1* | 8/2021 | Kapaldo ................ G16H 50/30 |

OTHER PUBLICATIONS

Abid, A., & Zou, J. (2019). Contrastive variational autoencoder enhances salient features. arXiv preprint arXiv:1902.04601. (Year: 2019).*

Mell et al., "The NIST Definition of Cloud Computing", NIST, Special Publication 800-145, Sep. 2011, 7 pages.

* cited by examiner

TREATMENT ADHERENCE SYSTEMS AND PROCESSES

BACKGROUND

Aspects of the present invention relate generally to managing healthcare and, more particularly, to treatment adherence systems and processes.

Public health organizations promote and facilitate health education and prevention of conditions. Adherence to prescribed treatments can help prevent conditions from becoming chronic.

SUMMARY

In a first aspect of the invention, there is a computer-implemented method including: receiving, by a computer device, an association of a prescribed treatment to a user; receiving, by the computer device, an image of the user; receiving, by the computer device, an image of treatment adherence by the user; determining, by the computer device, adherence to the prescribed treatment by analyzing the image of treatment adherence; and generating, by the computer device, a personalized visualization illustrating the determined adherence to the prescribed treatment by modifying the image of the user.

In another aspect of the invention, there is a computer program product including one or more computer readable storage media having program instructions collectively stored on the one or more computer readable storage media. The program instructions are executable to: train deep generative machine learning models to learn a physical progression of ailments and healing of the ailments for a prescribed treatment; receive an association of the prescribed treatment with a user; receive an image of the user; generate an initial visualization by modifying the image of the user using the deep generative machine learning models; send the initial visualization to a computing device of the user for display on the computing device of the user; receive an image of treatment adherence by the user; determine adherence to the prescribed treatment by extracting features from the image of treatment adherence and comparing the extracted features to known features of the prescribed treatment; and generate a modified personalized visualization based on the determined adherence and using the deep generative machine learning models.

In another aspect of the invention, there is system including a processor, a computer readable memory, one or more computer readable storage media, and program instructions collectively stored on the one or more computer readable storage media. The program instructions are executable to: train deep generative machine learning models to learn a physical progression of ailments and healing of the ailments for a prescribed treatment; receive an association of the prescribed treatment with a user; receive an image of the user commencing the prescribed treatment; generate an initial visualization by modifying the image of the user using the deep generative machine learning models to illustrate results of nonadherence to the prescribed treatment; send a message to the computing device of the user which contains the initial visualization; receive an image of treatment adherence by the user; determine adherence to the prescribed treatment by extracting features from the image of treatment adherence and comparing the extracted features to known features of the prescribed treatment; and generate a personalized visualization in response to adherence to the prescribed treatment.

BRIEF DESCRIPTION OF THE DRAWINGS

Aspects of the present invention are described in the detailed description which follows, in reference to the noted plurality of drawings by way of non-limiting examples of exemplary embodiments of the present invention.

DETAILED DESCRIPTION

Figure 1:
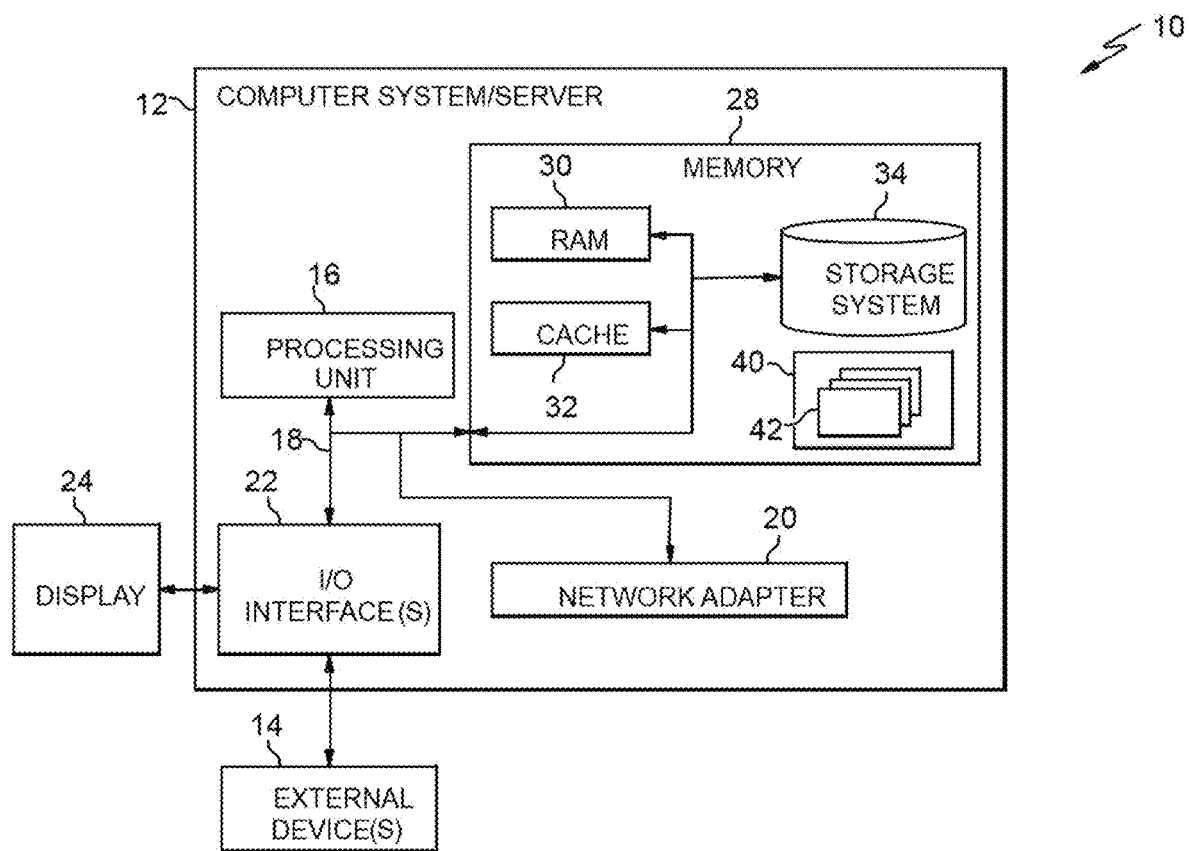
FIG. 1 depicts a cloud computing node according to an embodiment of the present invention.

Aspects of the present invention relate generally to managing healthcare and, more particularly, to treatment adherence systems and processes. In embodiments, treatment adherence improves by displaying a projected outcome to a user, such as a patient. In embodiments, a system generates and updates user models in view of treatment adherence and/or nonadherence. In this way, the systems and processes described herein illustrate to the user the results of treatment adherence and/or nonadherence.

Medical treatment adherence is critical for the treatment of chronic health conditions, e.g., diabetes, tuberculosis, etc. Accordingly, medical treatment nonadherence may have negative consequences. For example, a user may feel better after a day or two of taking antibiotics, and then stop adhering to the full course of treatment because they feel better. This treatment nonadherence can result in the development of antibiotic resistant strains and/or a worsening of symptoms, amongst other examples. For a community medical system, treatment nonadherence results in increased medical complications and costs, such as costs for reinitiating treatment for the user. For society as a whole, treatment nonadherence contributes to epidemics and development of 'super strong' bacteria, amongst other examples. Further, unused medicines diverted for illicit or unapproved purposes and flushed-down toilets or added to landfills results in problems with water, human and animal health. Accordingly, organizations interested in public health, public health entities, nongovernmental organizations (NGOs), and commercial healthcare providers desire to promote treatment adherence and facilitate health education to treat users with chronic conditions and to prevent relatively minor conditions deteriorating and becoming chronic.

The systems and processes described herein improve treatment adherence by monitoring user medicine intake, compliance, and treatment adherence, and by providing personalized visualizations back to the user. Embodiments include extracting images of treatment adherence and/or nonadherence for sending to a database for analysis. A system then generates personalized visualizations in view of the analysis to motivate the user for treatment adherence. In embodiments, the personalized visualizations illustrate consequences and risks of user nonadherence to a prescribed treatment. Alternatively, the personalized visualizations illustrate benefits of user compliance/adherence to treatment. In this way, a method and a system for personalized monitoring improves user treatment adherence by providing remote monitoring, validation, analysis and image generation.

In embodiments, the personalized visualizations contain hypothetical images of what could happen with respect to the user's body, either internally and/or externally. In this way, embodiments include automatically generating personalized visualizations showing effects of treatment nonadherence. In embodiments, the personalized visualizations are automatic illustrations or photographs depicting consequences of treatment nonadherence. For example, the personalized visualizations include one or more illustrations, photographs and/or composites-of-photographic face on an illustrated torso, all consistent with a specific disease focus.

In embodiments, the personalized visualizations are a visual representation which include a virtual pictorial and/or animated representation of an organ system or body part, and/or a photograph of one or more elements of the user. In one example for treatment nonadherence, pills from the prescribed treatment are not taken correctly, resulting in personalized visualizations for the user illustrating bodily dysfunction, organic and metabolic changes, and other personal appearance changes. In embodiments, the personalized visualizations are a photographic 'selfie' application which, as default, show consequences of treatment nonadherence.

In embodiments, the personalized visualizations include computer enhanced changes on the virtual pictorial and/or animated representation illustrating a malady to show consequences for treatment nonadherence. In one example, the personalized visualizations illustrate a modification of a picture of the user's own face and body to show the many changes resulting from nonadherence to treatment.

In embodiments, displaying of the personalized visualizations depicting medical consequences of nonadherence to the user occurs prior to treatment commencing, thereby illustrating a course of a non-treated disease, to motivate the user for full adherence to treatment. Accordingly, the systems and processes focus on user intrinsic motivation towards adherence, modification, and behavioral change by image and visualization generation, personalization, production and transmission.

In embodiments, a system generates the personalized visualizations using deep generative machine learning models, e.g., generative adversarial networks (GANs) or variational autoencoders (VAEs). In embodiments, a training phase includes training the deep generative machine learning models in view of images of the human body in different states of health and ailment. In this way, the deep generative machine learning models learn the physical progression of ailments and the reverse physical progression of healing. When new images, i.e., previously unseen data from the user, are presented, the deep generative machine learning models automatically generate a personalized visualization illustrating a hypothetical image or illustration in view of the training data.

In embodiments, a method includes an initial step of a healthcare provider prescribing a user with a course of medical treatment to treat a condition. In embodiments, the healthcare provider includes, for example and without limitation, a doctor, nurse, or other healthcare provider or practitioner. A second step includes associating the prescribed treatment with the user, the associating being performed utilizing a computing device, e.g., smartphone or other indicative device. In one example, the prescribed treatment includes a pill or inhaler having a barcode, QR-code or other specific identifier, which allows association of the prescribed treatment to the user using the computing device. A third step includes loading the prescribed treatment into a database. In one example, the database contains information about the user, the disease being treated, the prescribed treatment and treatment details including how to adhere to treatment.

In embodiments, a fourth step includes the user taking an image of themselves, e.g., a photograph of their face. At a fifth step, when the treatment commences or as part of treatment counselling, the user receives on their computing device a message showing a transformation of the image into a personalized visualization in view of treatment adherence and/or nonadherence as a preventative measure/education. In embodiments, generation of the personalized visualization uses deep generative machine learning models. In this way, the systems and processes described herein inform and motivate the user towards treatment adherence by showing them the results of treatment adherence and/or nonadherence prior to treatment commencing.

In embodiments, a sixth step includes the user adhering to the prescribed treatment by taking a pill, inhalation, injection, conducting a course of physical therapy or medical manipulation, etc. At a seventh step, the user captures treatment adherence by taking an image using a computing device, or other methods to note treatment adherence. An eighth step includes inputting treatment adherence data into a database for subsequent analysis.

In embodiments, when the treatment adherence module captures treatment adherence by photo, the treatment adherence module determines adherence to the prescribed treatment by analyzing the captured image to determine treatment adherence. In one example, a pill is geometrically well-defined and symmetrical, so photographic interpretation is straightforward.

In embodiments, if the treatment was properly and timely taken, no further action is done for that time period. Alternatively, if the treatment was not timely and properly taken, at a ninth step, the treatment adherence module sends messages having the personalized visualizations which show the consequences of treatment nonadherence to the user through the user's computing device. In one example, the personalized visualizations includes an illustration or photograph. In embodiments, the messages are periodic, on demand, or continually sent to the healthcare provider regarding treatment adherence and treatment nonadherence. If nonadherence of treatment continues, at a tenth step more messages are sent to the user and/or the healthcare provider. In embodiments, if it appears that significant amounts of medicine of the prescribed treatment are not used, further messages and personal follow-up occur to preclude improper diversion of the treatment medicine. Alternatively, if treatment adherence results, the facts of the prior nonadherence are saved.

In embodiments, a system for providing personalized images to a user includes an image capturing component to capture the user taking medicine of the prescribed treatment and an image visualization component that generates an augmentation of images of the user. Further, the system includes an association component that relates images of users with diseases at various stages, with the image visualization component generating augmented images of a typical user —including both current and future implications—with expected or potential physical, medical and operational changes due to pharmaceutical treatment nonadherence. Some embodiments include further refining of the image visualization component that generates augmented images of that particular user—including both current and future implications—with expected or potential —physical, medical and operational changes due to pharmaceutical treatment nonadherence, in view of the particulars of the user's case.

Implementations of the invention allow for the practical application of user treatment adherence. In embodiments, the systems and processes described herein utilize deeply rooted computing technology including deep generative machine learning models, e.g., generative adversarial networks (GANs) or variational autoencoders (VAEs), to generate personalized visualizations for the user. The personalized visualizations are then sent to the user for treatment adherence motivation. In one example, the personalized visualizations include computer enhanced changes on a virtual pictorial and/or animated representation illustrating a negative change in condition or other malady to show consequences for treatment nonadherence. In this way, the training of the deep generative machine learning models in view of a physical progression of ailments and the reverse physical progression of healing assists in achieving user treatment adherence. Accordingly, the systems and processes described herein provide the practical application of treatment adherence by having deep generative machine learning models learn physical progression of ailments and the reverse physical progression of healing to generate personalized visualizations for the user.

In addition, the steps for treatment adherence are unconventional. In embodiments, when a treatment is prescribed to a user, a method of improving treatment adherence includes: a) associating the prescribed treatment with the user; b) loading the prescribed treatment into a database; c) taking an image of the user; d) sending a message to the user showing an image transformation into a personalized visualization using deep generative machine learning models in view of treatment adherence and/or nonadherence as a preventative measure/education when treatment commences or as part of treatment counselling; e) capturing information indicative of treatment adherence by the user; f) analyzing the captured information to determine treatment adherence; g) sending messages which include personalized visualizations showing consequences of treatment nonadherence to the user if the treatment was not properly adhered to and/or timely taken; and h) if nonadherence of treatment continues, sending more messages to the user and/or sending messages to the healthcare provider. In view of this arrangement of steps, the systems and processes motivate the user to adhere to the prescribed treatment. Accordingly, the unconventional arrangement of steps disclosed herein allow for treatment adherence, thereby providing a solution to the problem of treatment nonadherence.

It should be understood that, to the extent implementations of the invention collect, store, or employ personal information provided by, or obtained from, individuals (for example, user information and treatment information submitted by a user to a computing device), such information shall be used in accordance with all applicable laws concerning protection of personal information. Additionally, the collection, storage, and use of such information may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium or media, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
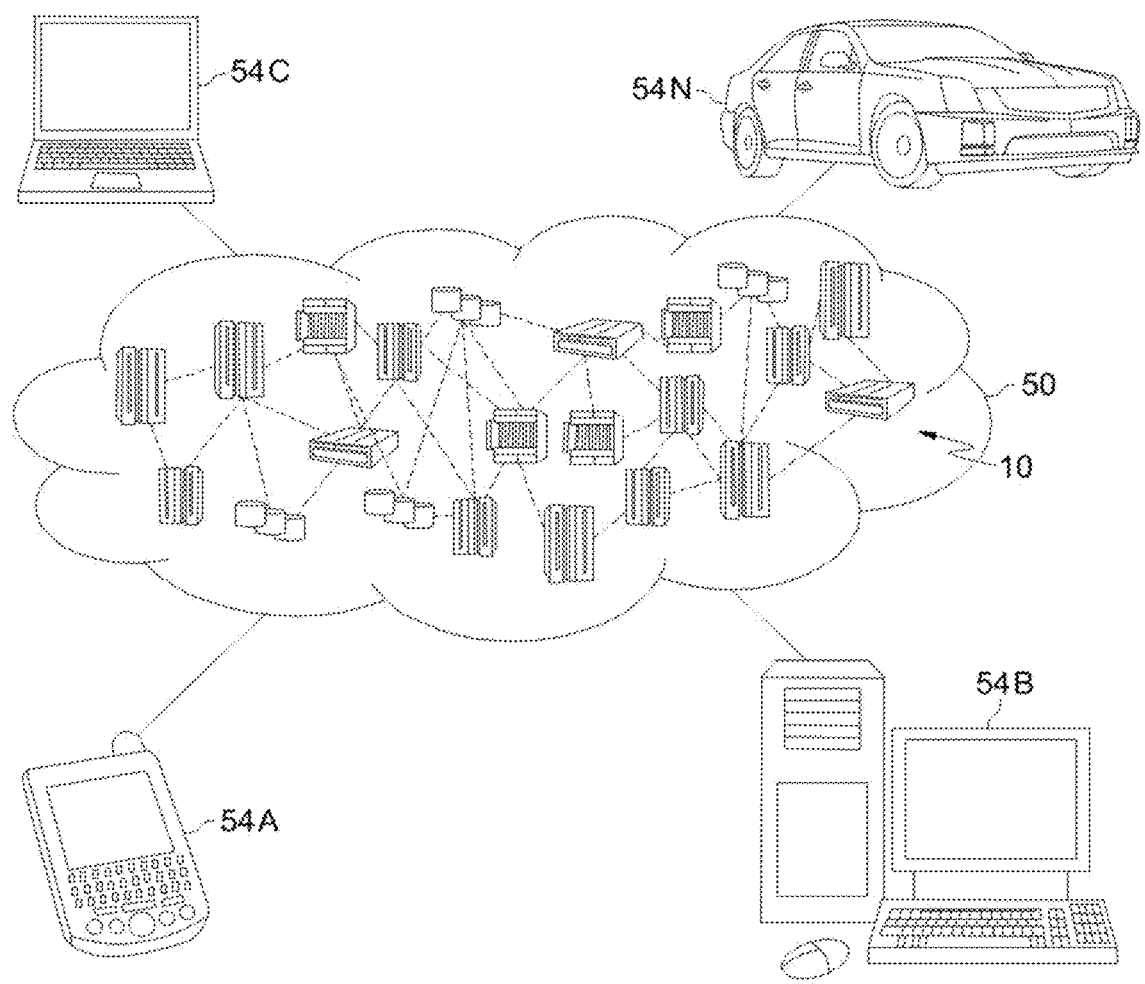
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
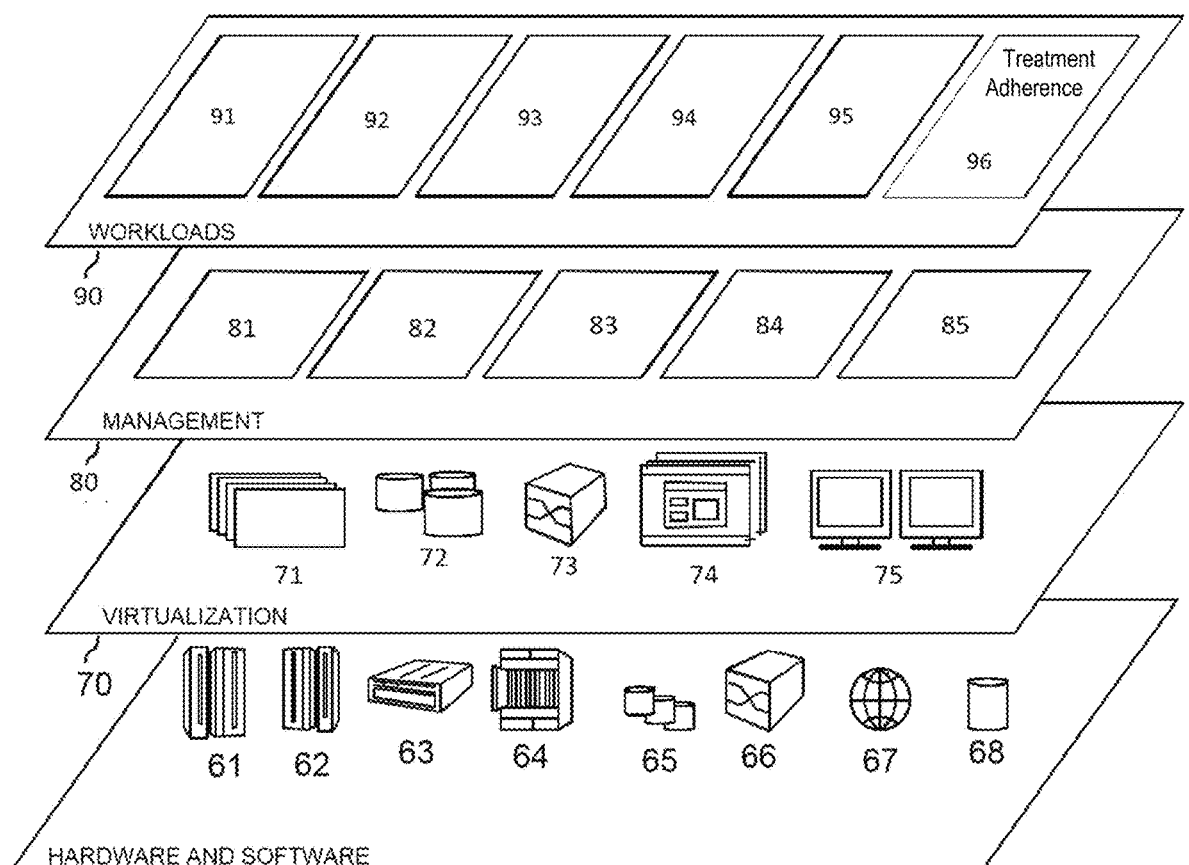
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and treatment adherence 96.

Implementations of the invention may include a computer system/server 12 of FIG. 1 in which one or more of the program modules 42 are configured to perform (or cause the computer system/server 12 to perform) one of more functions for the treatment adherence 96 of FIG. 3. For example, the one or more of the program modules 42 may be configured to: a) associate a prescribed treatment to a user using a computing device of the user; b) load the prescribed treatment into a database; c) take an image of the user using their computing device; d) send a message to the user through their computing device showing an image transformation into a personalized visualization using deep generative machine learning models in view of treatment adherence and/or nonadherence as a preventative measure/education when treatment commences or as part of treatment counselling; e) capture treatment adherence by the user using the computing device; f) analyze the captured image to determine treatment adherence; g) send messages which include personalized visualizations showing consequences of treatment nonadherence to the user through the computing device if treatment nonadherence and/or untimely; and h) if nonadherence of treatment continues, send more messages to the user and/or sending messages to a healthcare provider who prescribed the treatment.

Figure 4:
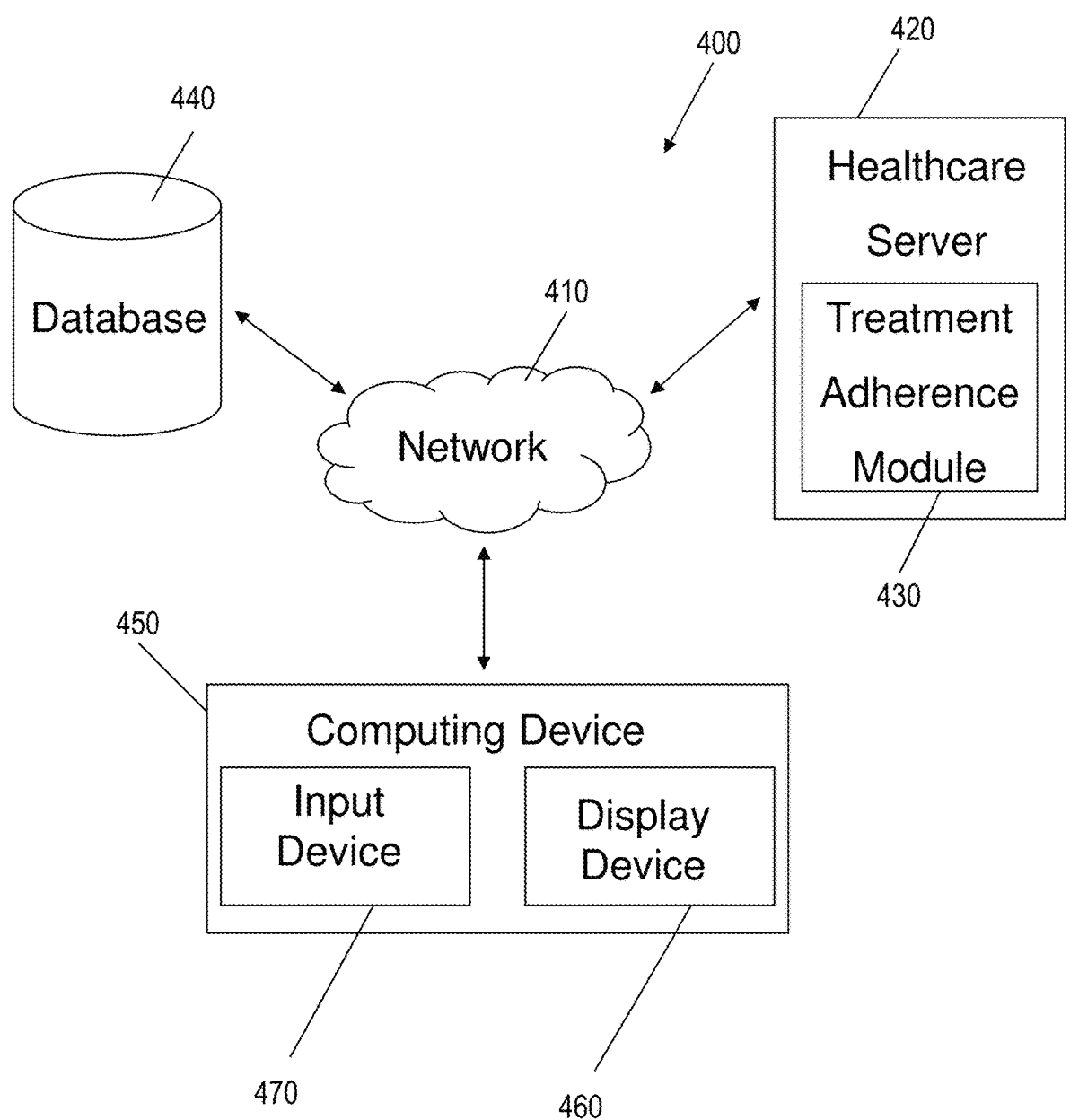
FIG. 4 shows a block diagram of an exemplary environment in accordance with aspects of the invention.

FIG. 4 shows a block diagram of an exemplary environment 400 in accordance with aspects of the invention. In embodiments, the environment 400 includes network 410, healthcare server 420, database 440 and computing device 450. In embodiments, the healthcare server 420 comprises a treatment adherence module 430, which comprises one or more program modules such as program modules 42 described with respect to FIG. 1. The healthcare server 420 may include additional or fewer modules than those shown in FIG. 4. In embodiments, separate modules may be integrated into a single module. Additionally, or alternatively, a single module may be implemented as multiple modules. Moreover, the quantity of devices and/or networks in the environment is not limited to what is shown in FIG. 4. In practice, the environment may include additional devices and/or networks; fewer devices and/or networks; different devices and/or networks; or differently arranged devices and/or networks than illustrated in FIG. 4.

The network 410 is any one or more networks and, in one example, corresponds to the cloud computing environment as described in FIG. 2. The computing device 450 may be a mobile computing device, e.g., smartphone, smartwatch, tablet, laptop etc., and includes one or more components of the computer system 12 of FIG. 1. The computing device 450 associates a prescribed treatment, captures treatment adherence and receives messages containing personalized visualizations in view of treatment adherence and/or nonadherence. In embodiments, the computing device 450 includes a display device 460 for displaying the messages and an input device 470 for associating the prescribed treatment and capturing treatment adherence. In one example, the input device 470 is a camera and/or a keyboard or other input device.

In embodiments, the processes are into two phases: 1) prior to commencing treatment; and 2) after commencing treatment. The first phase prior to commencing treatment phase begins with a training phase. In embodiments, the training phase includes training deep generative machine learning models, such as generative adversarial networks (GANs) or variational autoencoders (VAEs), on images of the human body in different states of health and ailment stored in the database 440, thus training the deep generative machine learning models the physical progression of ailment and the reverse of ailment, i.e., healing.

In embodiments, the training of the deep generative machine learning models occurs in view of relatively large datasets of healthcare information. These datasets include information regarding medical conditions, prescribed treatments addressing the condition, results of adherence to the prescribed treatment and consequences of nonadherence to the prescribed treatment. For example, deep generative machine learning models using GANs analyze images within the datasets for training. For example, the dataset may include images of ailments illustrating the condition of a particular skin malady, images of the type of medicine of the prescribed treatment for treating that particular skin malady, images illustrating beneficial changes in the skin malady condition in view of treatment adherence and images illustrating consequences of nonadherence to treatment.

In embodiments, analysis of images includes assigning coordinates to features within the images. For example, the treatment adherence module 430 assigns coordinates to a feature of the particular skin malady on the skin of a user. As the user adheres to the prescribed treatment, images in the dataset illustrate a reduction in the area of concern for the skin malady. Accordingly, the treatment adherence module 430 updates the coordinates for the skin malady, thereby training the deep generative machine learning models in view of a reduction of the area of concern in view of treatment adherence. Alternatively, images in the dataset illustrate that the area of concern for the skin malady increases as treatment nonadherence occurs.

In embodiments, as the GANs analyze images, the treatment adherence module 430 generates feedback regarding the images and stores the feedback in the database 440. Accordingly, as the deep generative machine learning model analyzes more images, feedback increases. In this way, as the volume of training data increases, the accuracy of the deep generative machine learning models improves. In embodiments, the deep generative machine learning models utilize VAEs for training. For example, the training of the deep generative machine learning models using VAEs includes reconstructing datasets in view of the information within the original datasets using autoencoding and decoding. In embodiments, as reconstruction occurs over many instances, the treatment adherence module 430 generates feedback regarding the reconstruction, with the treatment adherence module 430 storing the reconstruction feedback in the database 440. Accordingly, as more reconstructions of datasets occur, feedback increases to improve accuracy of the deep generative machine learning models.

In view of the training, when the deep generative machine learning models receive new images from the user, i.e., previously unseen data, the deep generative machine learning models automatically generate personalized visualizations illustrating a hypothetical image or other illustration with respect to the particulars of the user's case in view of the training data. Examples of personalized visualizations include a virtual pictorial and/or animated representation of an organ system or body part, and/or a photograph of one or more elements of the user. In one example, the personalized visualization is a photographic 'selfie' which now shows a malady resulting from treatment nonadherence.

In embodiments, the virtual pictorial includes computer enhanced items including a negative change in condition or other malady to show consequences for treatment nonadherence. Alternatively, for treatment adherence, virtual pictorial includes computer enhanced items showing improvement in the condition. For example, a reduction in an area of a particular skin malady in view of treatment adherence. In this way, the treatment adherence module 430 includes an image visualization component which generates augmented images of a typical user —including both current and future implications—with expected or potential physical, medical and operational changes due to pharmaceutical treatment nonadherence. In embodiments, the treatment adherence module 430 includes association component that relates images of users with diseases at various stages.

After the training phase, the user consults with a healthcare provider to treat their condition. During the consultation, the healthcare provider prescribes the user a course of treatment to treat the condition. In view of the prescribed treatment, the user then associates the prescribed treatment with the user using the computing device 450. In embodiments, the user associates the prescribed treatment to themselves using the input device 470. For example, the prescribed treatment includes consuming a pill and/or using a treatment device, e.g., an inhaler, to address the condition. In embodiments, the pill and/or treatment device includes a barcode, a quick response code (QR-code) and/or other specific identifier. In one example, the user associates the prescribed treatment using the computing device 450 by taking a picture of the pill or scanning the barcode using the input device 470.

In another example of associating the prescribed treatment with the user, the input device 470 is a keyboard and the user manually associates the prescribed treatment to themselves by entering information regarding the prescribed treatment using the keyboard. In another example, the prescribed treatment comes with a universal serial bus (USB) storage device containing information regarding the prescribed treatment, and the user pairs the USB flash drive with the computing device 450 to associate the prescribed treatment using the computing device 450. In embodiments, the healthcare server receives the association of the user with the prescribed treatment.

In embodiments, the user and/or the healthcare provider loads information regarding the user, ailment/disease/medical condition being treated by the prescribed treatment and the prescribed treatment into the database 440. In one example, the healthcare provider manually enters the information into the database 440 at the time of consultation so that the database 440 contains the information regarding the user, ailment/disease/medical condition being treated by the prescribed treatment and the prescribed treatment prior to associating the prescribed treatment using the computing device 450. In embodiments, loading of the information into the database 440 occurs at the same time as, before, or after the association of the prescribed treatment using the computing device 450. In this way, the healthcare provider prescribes the user a course of treatment, with the user associating the prescribed treatment with themselves into the database 440 using the computing device 450. Accordingly, the database contains information about the prescribed treatment and the user.

In embodiments, the user captures an image of themselves using the computing device 450. In one example, the input device 470 is a camera or other image capturing component, with the user taking a photograph of an element of their body using the input device 470. In embodiments, the element is a face of the user or other region of their body that is the subject of the prescribed treatment. In embodiments, the network 410 sends the image of the user to the database 440 for storage. Alternatively, the healthcare provider captures the image of the user at the consultation. In embodiments, the image of the user is a clear descriptive image of the user showing the user's own face and body and condition being treated.

In embodiments, the treatment adherence module 430 modifies the image of the user to generate an initial personalized visualization for the user as a preventative measure/education. In one example, the deep generative machine learning models augment the image of the user to show the beneficial results of adhering to the prescribed treatment. In another example, the deep generative machine learning models augment the image of the user to show the negative results of nonadherence of the prescribed treatment. In this way, the treatment adherence module 430 informs and motivates the user towards treatment adherence by showing the user on the computing device 450 hypothetical images of what could happen in their body (internally or externally) if they take the medicine correctly and if they do not adhere to the treatment. In embodiments, the initial personalized visualization is an automatically generated illustration or photograph for display on the display device 460 of the computing device 450. In one example, the initial personalized visualization includes a virtual pictorial and/or animated representation of an organ system or body part, and/or a photograph of one or more elements of the user which now includes computer enhanced items such as a negative change in condition or other malady to show treatment nonadherence consequences.

In embodiments, the second phase occurs after commencing treatment and begins with the user capturing treatment adherence, e.g., medicine consumption, as an image on the registered computing device 450. For example, the user captures the image of treatment adherence by taking a photograph of the medicine being consumed using the input device 470 of the computing device 450. In one example, the user takes a photograph of performing an injection in accordance with their prescribed treatment. In another example, the user takes a photograph of a pill of the prescribed treatment prior to consumption. In this way, when the user takes a pill, inhalation, injection, etc., or a course of physical therapy or medical manipulation, the user takes a picture of the treatment adherence on the computing device 450, or otherwise notes treatment adherence. In one example, the user notes treatment adherence by manually entering information into the input device 470 of the computing device 450.

Following the capture of treatment adherence, the computing device 450 sends through the network 410 the captured images of treatment adherence to the database 440. In embodiments, the treatment adherence module 430 recognizes the user and the medical treatment from the information previously loaded into the database by the user and/or the healthcare provider and updates the information in the database. The treatment adherence module 430 then determines whether the user adheres to and complies with the prescribed treatment correctly. For example, if treatment adherence was captured by photograph, the treatment adherence module 430 determines adherence to the prescribed treatment by analyzing the features in the photograph.

In embodiments, the treatment adherence module 430 utilizes photographic interpretation techniques to determine adherence to the prescribed treatment. In one example, a pill is generally geometrically well-defined and symmetrical, so photographic interpretation is straightforward by analyzing the geometry and the symmetry of the pill within the image. In this way, the treatment adherence module 430 extracts geometrical features and symmetrical features of the pill from the image by photographic interpretation. In embodiments, the database 440 includes information regarding the prescribed treatment. In this way, the treatment adherence module compares the features extracted from the image of treatment adherence to known features of the prescribed treatment. In another example, items such as inhalers often have counters to show a number of inhalations taken, while hypodermic needles have indicia that indicate an amount of medicine used. Accordingly, in addition to comparing extracted features to known features, the photographic interpretation techniques extract numbers representing amounts of medicine of the prescribed treatment. In this way, the system uses photographic interpretation techniques for recognition that an inhalation has been taken in view of the counter on the inhaler device by extracting number features from the inhaler device. In embodiments, determination of prescribed treatment adherence occurs prior to a next pill or other course of action being due. If the pill or other course of action was properly and timely taken, i.e., medical adherence as per prescribed treatment, the treatment adherence module 430 performs no further action for that time period.

In embodiments, if the medication was not timely and properly taken, i.e., nonadherence to the prescribed treatment, the treatment adherence module 430 messages the computing device 450 about the nonadherence to the prescribed treatment. In one example, the message is a short message service message containing the personalized visualization. In another example, the message is an email message containing the personalized visualization. In this way, the messages include a personalized visualization illustrating manipulations and consequences of nonadherence to the prescribed treatment. Alternatively, if the user adheres to the prescribed medical treatment, the treatment adherence module 430 sends the user a message containing a personalized visualization illustrating the beneficial results of adhering to the prescribed treatment.

In embodiments, the personalized visualization includes a generated illustration, photograph, virtual pictorial and/or animated representation of an organ system or body part of the user showing the consequences of nonadherence to the prescribed treatment. The consequences shown in the personalized visualization include computer enhanced items such as a negative change in condition or other malady to illustrate treatment nonadherence consequences. In one example, the personalized visualization is a photographic 'selfie' which now shows a negative change in condition or other malady because of the nonadherence to the prescribed treatment. Alternatively, if the treatment adherence module 430 generates a message in view of adherence to the prescribed treatment, the treatment adherence module 430 modifies the personalized visualization to show the beneficial results of adhering to the treatment. For example, the personalized visualization illustrates a reduction in symptoms in view of treatment adherence. In embodiments, the messages are periodic, on-demand and/or continually sent to the user and/or the healthcare provider to inform of nonadherence with the prescribed treatment.

In embodiments, the treatment adherence module 430 generates the personalized visualization by modifying the image of the user captured prior to commencing treatment. The treatment adherence module 430 uses the deep generative machine learning models to augment the image of the user to show the consequences of nonadherence to the prescribed treatment. In embodiments, training of the deep generative machine learning models occurs prior to the user commencing treatment in view of images of the human body in different states of health and ailment. In this way, the deep generative machine learning models learn the physical progression of ailments and the reverse physical progression of healing. In view of the image of the user captured prior to treatment commencing, the deep generative machine learning models automatically generate a personalized visualization illustrating a hypothetical image or illustration in view of the training data.

In embodiments, if noncompliance/nonadherence to the prescribed treatment continues to occur, further messages are sent to the user and/or the healthcare provider informing of the treatment nonadherence. In one example, the healthcare provider calls and/or performs a follow-up with the user regarding the nonadherence to the prescribed treatment. In embodiments, these messages include personalized visualizations further illustrating the consequences of nonadherence to the prescribed treatment. Further, if significant amounts of the medicine of the prescribed treatment were not used, message and personal follow-up occur to preclude improper diversion of the medicine of the prescribed treatment, e.g., medicine. In embodiments, at each stage of adherence and nonadherence of the prescribed treatment, the treatment adherence module 430 stores the adherence data and within the database 440. In one example, if adherence results after the user receiving the message, the treatment adherence module 430 stores the facts of the prior nonadherence and new adherence within the database 440.

Figure 5:
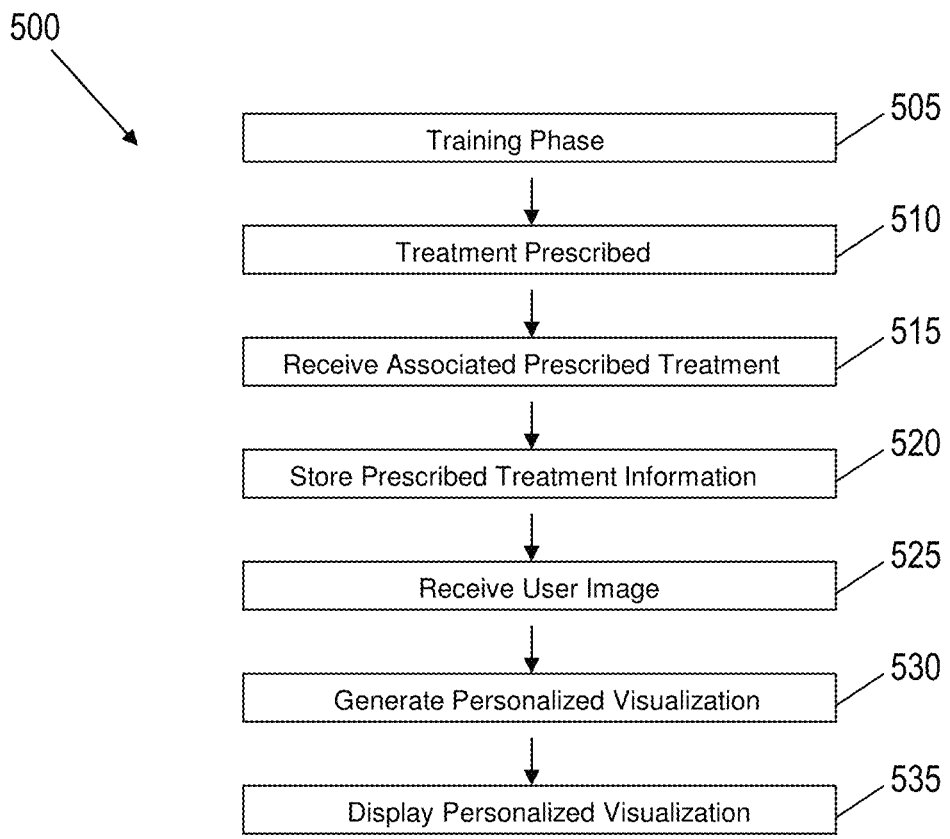
FIG. 5 shows a flowchart of an exemplary method prior to commencing treatment in accordance with aspects of the invention.

FIG. 5 shows a flowchart 500 of an exemplary method which illustrates a first phase which occurs prior to the commencement of treatment. Steps of the method may be carried out in the environment of FIG. 4 and are described with reference to elements depicted in FIG. 4. At step 505, the system trains deep generative machine learning models of the treatment adherence module 430 with respect to images of the human body in different states of health and ailment, thus training the deep generative machine learning models includes the physical progression of ailment and the reverse of ailment, i.e., healing. In embodiments, and as described with respect to FIG. 4, training of the deep generative learning models includes analyzing images showing health and ailment by assigning coordinates to the features within the images. As more images are analyzed, the feedback regarding analysis of the features increases.

At step 510, the user consults with the healthcare provider to treat their condition. In embodiments, the healthcare provider prescribes the user a course of treatment to treat the condition. At step 515, the treatment adherence module 430 receives association between the user and the prescribed treatment. In embodiments, and as described with respect to FIG. 4, the user associates the prescribed treatment with themselves using the computing device through the input device 470. For example, the pill and/or treatment device of the prescribed treatment includes a barcode, a quick response code (QR-code) and/or other specific identifier. In one example, the user associates the prescribed treatment using the computing device 450 by scanning the barcode using the input device 470.

At step 520, the system stores information of the prescribed treatment in the database 440. In embodiments, loading and storing the treatment information into the database 440 includes information regarding the user, ailment/disease/medical condition being treated by the prescribed treatment, and the prescribed treatment. In one example, the healthcare provider manually enters the information into the database 440 by the healthcare provider at the time of consultation. At step 525, the healthcare server 420 receives an image of the user. In embodiments, and as described with respect to FIG. 4, the computing device 450 captures the user image through the input device 470 and the healthcare server 420 server receives the image through the network 410.

At step 530, the treatment adherence module 430 generates a personalized visualization for the user. In embodiments, and as described with respect to FIG. 4, generation of the personalized visualization includes a modification of the image of the user by the treatment adherence module 430 using the deep generative machine learning models. At step 535, the treatment adherence module 430 displays the personalized visualization to the user through the display device 460 of the computing device 450. In embodiments, and as described with respect to FIG. 4, the treatment adherence module 430 delivers the personalized visualization as a message, e.g., short message service (SMS) message, which contains the personalized visualization.

Figure 6:
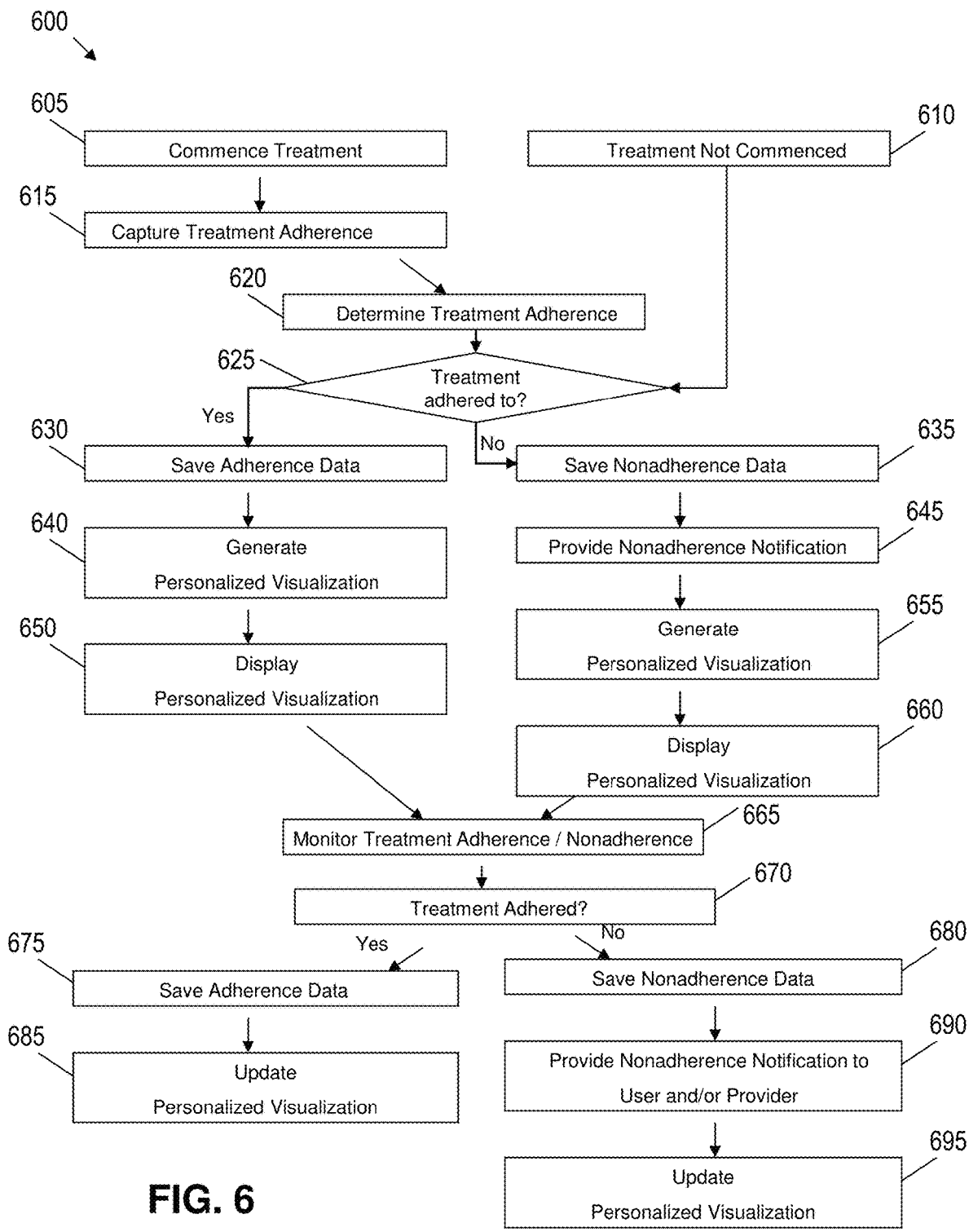
FIG. 6 shows a flowchart of an exemplary method after commencing treatment in accordance with aspects of the invention.

FIG. 6 shows a flowchart 600 of an exemplary method which illustrates a second phase which occurs after commencing treatment. Steps of the method may be carried out in the environment of FIG. 4 and are described with reference to elements depicted in FIG. 4.

At step 605, the user commences their prescribed treatment prescribed at step 510 from FIG. 5. Alternatively, at step 610, treatment is not commenced. In embodiments, if the user commences the prescribed treatment, the process proceeds to step 615 in which the user captures an image of treatment adherence using their computer device. In one example, and as described with respect to FIG. 4, the user takes a photograph using the input device 470 of them performing an injection in accordance with their prescribed treatment. In another example, the user takes the photograph using the input device 470 of a pill of the prescribed treatment prior to consumption. Step 615 may include the treatment adherence module 430 receiving the image of treatment adherence from the computer device.

At step 620, the treatment adherence module 430 determines treatment adherence of the user with respect to the prescribed treatment. In embodiments, step 620 includes the treatment adherence module 430 analyzing the image of treatment adherence to determine whether the user adhered to the prescribed treatment. For example, and as described with respect to FIG. 4, the treatment adherence module 430 determines adherence to the prescribed treatment by analyzing and extracting the features in the image of treatment adherence. In embodiments, the treatment adherence module 430 compares the features extracted from the image of treatment adherence to known (e.g., predefined) features of the prescribed treatment (e.g., a shape of a pill, a color of a pill, indicia on a pill, a bar code on a device such as a syringe or inhaler, indicia indicative of an amount of medicine used, such as a counter on an inhaler, etc.). By analyzing the image data in this manner, the system determines a degree to which the user adhered to the prescribed treatment. In embodiments, the degree is binary with only two possible determinations: the user either fully adhered to the prescribed treatment or the user did not adhere to the prescribed treatment.

In the event the system determines at step 620 that the treatment was adhered to (i.e., step 625=Yes), then at step 630 the treatment adherence module 430 saves adherence data (e.g., data defining the adherence) in the database 440. In the event the system determines at step 620 that the treatment was not adhered to (i.e., step 625=No), then at step 635 the treatment adherence module 430 saves nonadherence data in the database 440.

At step 640, the treatment adherence module 430 generates a personalized visualization. In embodiments, and as described with respect to FIG. 4, the treatment adherence module 430 modifies the image of the user (e.g., the image from step 525) to illustrate the beneficial results of the user adhering to the prescribed treatment. At step 650, the treatment adherence module 430 displays the personalized visualization to the user. In embodiments, and as described with respect to FIG. 4, the displaying comprises the treatment adherence module 430 sending the personalized visualization to the computing device 450, which displays the personalized visualization on the display device 460.

Alternatively, at step 645, the treatment adherence module 430 provides the user a notification regarding the nonadherence of the prescribed treatment. In embodiments, and as described with respect to FIG. 4, this includes the treatment adherence module 430 sending a message to the computing device 450 informing the user of their nonadherence to the prescribed treatment.

At step 655, the treatment adherence module 430 generates a personalized visualization that illustrates effects of nonadherence to the prescribed treatment. In embodiments, and as described with respect to FIG. 4, the personalized visualization includes an illustration, photograph, virtual pictorial and/or animated representation of an organ system or body part of the user showing the consequences of nonadherence to the prescribed treatment using the deep generative machine learning models. In embodiments, and as described with respect to FIG. 4, the personalized visualization includes computer enhanced items such as a negative change in condition or other malady to show treatment nonadherence consequences. In one example, the personalized visualization is a photographic 'selfie' which now shows a negative change in condition or other malady because of the nonadherence to the prescribed treatment. In embodiments, and as described with respect to FIG. 4, the treatment adherence module 430 sends the message of step 645 prior to or concurrently with the personalized visualization generated at step 655

At step 660, the treatment adherence module 430 displays the personalized visualization to the user on the computing device 450 through the display device 460. In embodiments, and as described with respect to FIG. 4, the displaying comprises the treatment adherence module 430 sending the personalized visualization to the computing device 450, which displays the personalized visualization on the display device 460.

At step 665, the treatment adherence module 430 continues to monitor treatment adherence and/or nonadherence by the user. In embodiments, and as described with respect to FIG. 4, this includes the treatment adherence module 430 repeating the steps of 605-660 depending on adherence or nonadherence to the prescribed treatment.

At step 670, the treatment adherence module 430 determines treatment adherence. In embodiments, and as described with respect to FIG. 4, this includes the treatment adherence module 430 receiving a further image of treatment adherence and analyzing this further image of treatment adherence.

At step 675, in view of treatment adherence, the treatment adherence module 430 saves the adherence data in the database 440. In embodiments, and as described with respect to FIG. 4, the treatment adherence module 430 stores the adherence data into the database 440. Alternatively, if treatment is not adhered, the treatment adherence module 430 saves the nonadherence data into the database 440 at step 680. In embodiments, and as described with respect to FIG. 4, this includes the treatment adherence module 430 storing the nonadherence data into the database 440.

At step 685, the treatment adherence module 430 updates the previously generated personalized visualization (e.g., from step 640 or step 655) to illustrate the effects of adherence to the prescribed treatment as determined at steps 665 and 670. In embodiments, and as described with respect to FIG. 4, this includes the treatment adherence module 430 modifying the previously generated personalized visualization to illustrate beneficial results of continuing adherence to the prescribed treatment.

At step 690, if the user continues to not adhere to the prescribed treatment, the treatment adherence module 430 provides a nonadherence notification to the user and/or the healthcare provider concerning the nonadherence. In embodiments, and as described with respect to FIG. 4, the message includes nonadherence data. At step 695, the treatment adherence module 430 updates the personalized visualization (e.g., from step 640 or step 655) to illustrate the effects of nonadherence to the prescribed treatment as determined at steps 665 and 670. In embodiments, and as described with respect to FIG. 4, the treatment adherence module 430 modifies the previously generated personalized visualization to show the consequences of further nonadherence to the prescribed treatment. In one example, the personalized visualization shows the user's condition getting worse.

Figure 7:
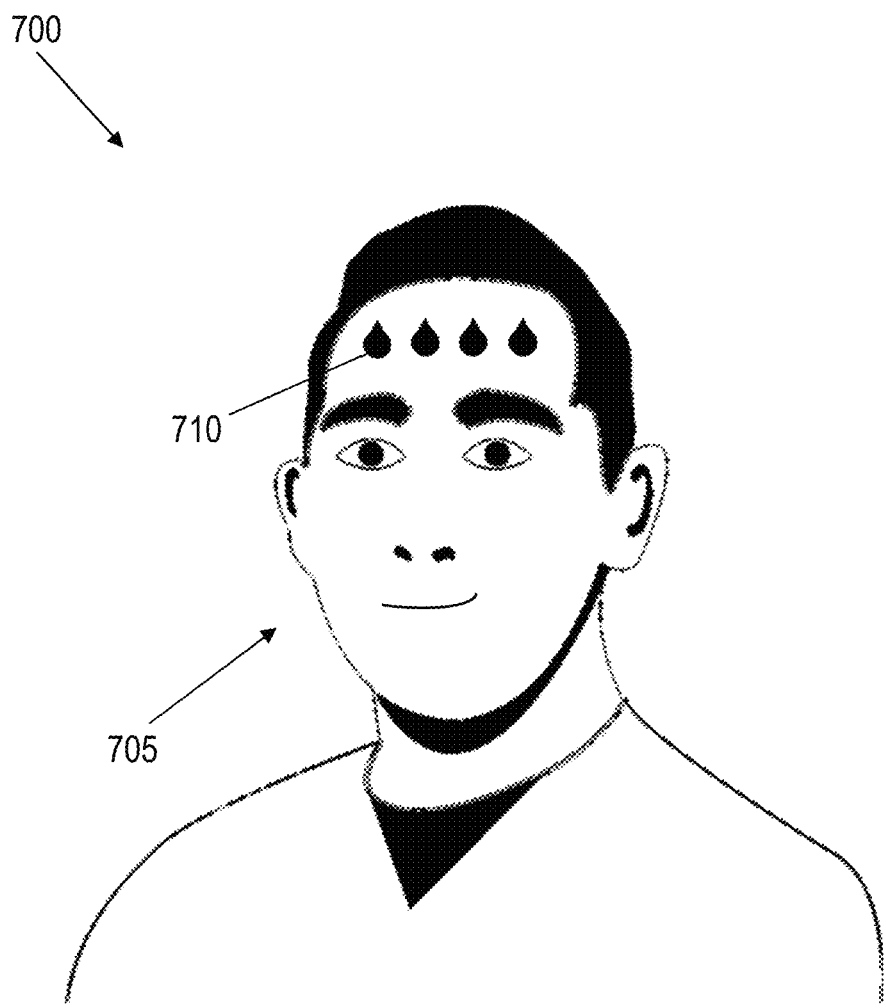
FIG. 7 shows an exemplary model of a user prior to commencing treatment in accordance with aspects of the invention.
Figure 8A:
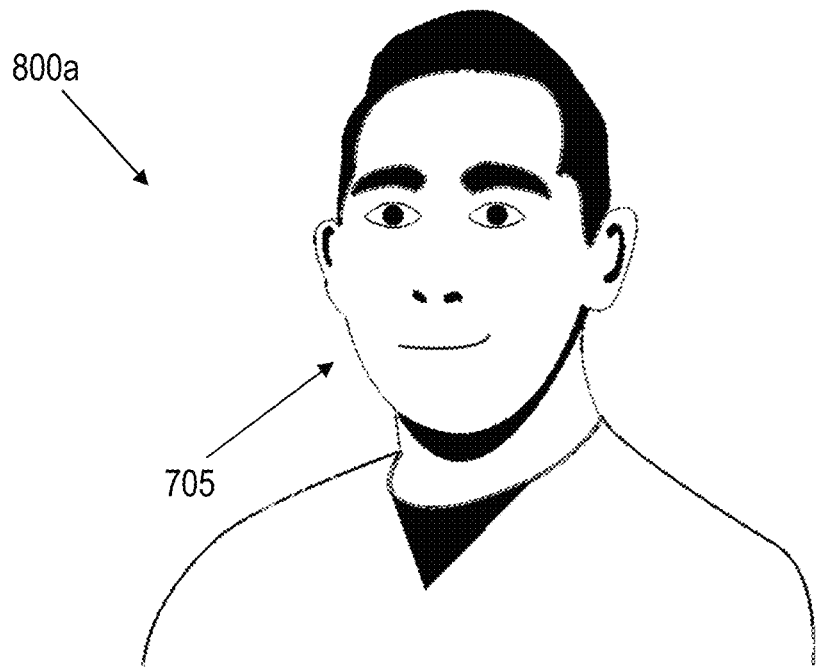
FIGS. 8A and 8B show exemplary models of the user in view of treatment adherence and nonadherence in accordance with aspects of the invention.
Figure 8B:
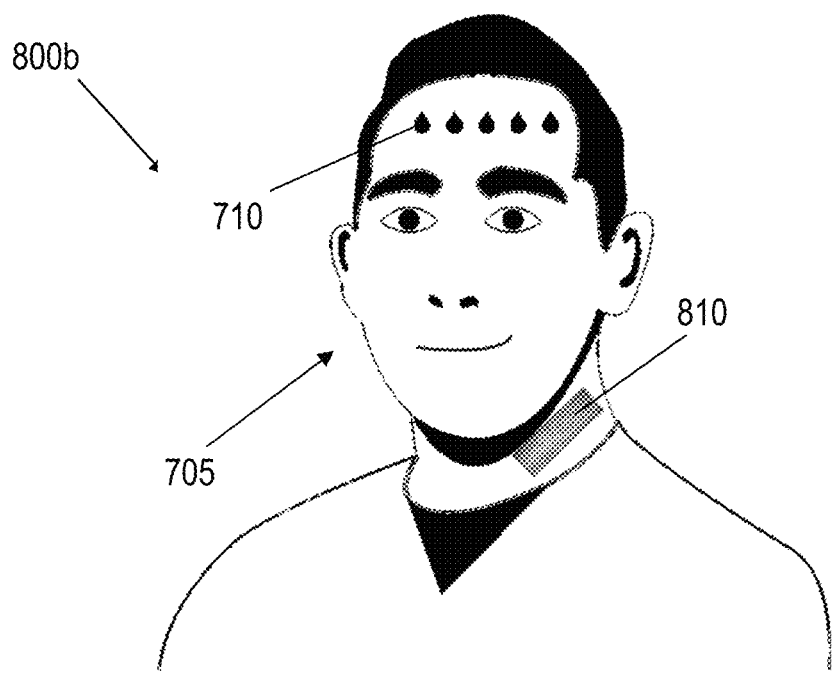

FIG. 7 illustrates an image 700 of a user 705 with a medical condition 710, e.g., fever. In embodiments, capturing of the image occurs prior to treatment commencing. FIGS. 8A and 8B illustrate personalized visualizations in view of adherence or nonadherence to the prescribed treatment. In FIG. 8A, the user 705 adheres to the prescribed treatment. Accordingly, the adherence personalized visualization 800a illustrates the beneficial results of adherence to the prescribed treatment. In embodiments, the treatment adherence module 430 indicates beneficial results by removing the medical condition 710. Alternatively, in FIG. 8B, the user 705 does not adhere to the prescribed treatment. Accordingly, the nonadherence personalized visualization 800b illustrates the consequences of nonadherence to the prescribed treatment. In embodiments, the user not only still has the medical condition 710, but now has a new medical condition 810 resulting from the nonadherence to the prescribed treatment. In embodiments, the treatment adherence module 430 generates the personalized visualizations 800a and 800b prior to the user commencing treatment and/or after the user commences treatment.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/ or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   receiving, by a computer device, an association of a prescribed treatment of an ailment to a user;
   receiving, by the computer device, an image of the user;
   receiving, by the computer device, an image of treatment adherence by the user;
   determining, by the computer device, adherence to the prescribed treatment by analyzing the image of treatment adherence, wherein the determining comprises extracting features from the image of treatment adherence using photographic interpretation techniques and comparing the extracted features to known features of the prescribed treatment; and
   generating, by the computer device, a personalized visualization illustrating the determined adherence to the prescribed treatment by augmenting the image of the user in the personalized visualization with images of the ailment of the user based on the determined adherence,
   wherein the generating the personalized visualization is performed using a deep generative machine learning model trained with images of treatment adherence, the deep generative machine learning model basing the personal visualization on the image of treatment adherence that is previously unseen data, and the deep generative machine learning model utilizing variational autoencoders that reconstruct datasets using autoencoding and decoding in view of information within the datasets.

2. The method of claim 1, further comprising sending, by the computer device, a message containing the personalized visualization to the user via a user device.

3. The method of claim 1, further comprising storing, by the computer device, adherence data defining the determined adherence to the prescribed treatment in a database.

4. The method of claim 1, further comprising generating, by the computer device, an initial visualization showing results of adherence or nonadherence to the prescribed treatment prior to a capturing of the image of treatment adherence.

5. The method of claim 1, wherein the analyzing the image of the treatment adherence includes analyzing a geometry and a symmetry of a pill within the image.

6. The method of claim 1, further comprising comparing, by the computer device, the extracted features to known features of the prescribed treatment by extracting number features from the image that indicate an amount of medicine of the prescribed treatment.

7. The method of claim 1, further comprising modifying, by the computer device, the personalized visualization in view of nonadherence to the prescribed treatment by augmenting the personalized visualization with images of a disease of the user at various stages, the disease being associated with the prescribed treatment.

8. The method of claim 2, further comprising monitoring, by the computer device, further adherence or nonadherence to the prescribed treatment after the sending the message containing the personalized visualization to the user.

9. The method of claim 8, further comprising training, by the computer device, the deep generative machine learning model by assigning coordinates to features within images of ailments.

10. The method of claim 9, further comprising providing, by the computer device, a nonadherence notification to a provider of the prescribed treatment in response to the nonadherence to the prescribed treatment.

11. The method of claim 10, wherein the personalized visualization includes computer enhanced items showing results of the determined adherence to the prescribed treatment.

12. The method of claim 11, wherein the deep generative machine learning model includes generative adversarial networks.

13. A computer program product comprising one or more computer readable storage media having program instructions collectively stored on the one or more computer readable storage media, the program instructions executable to:
   train deep generative machine learning models to learn a physical progression of ailments and healing of the ailments for a prescribed treatment;
   receive an association of the prescribed treatment with a user;
   receive an image of the user;
   generate an initial visualization by modifying the image of the user using the deep generative machine learning models;
   send the initial visualization to a computing device of the user for display on the computing device of the user;
   receive an image of treatment adherence by the user;
   determine adherence to the prescribed treatment by extracting features from the image of treatment adherence and comparing the extracted features to known features of the prescribed treatment; and
   generate a modified personalized visualization based on the determined adherence and augmenting the image of the user with a hypothetical image or illustration based on the deep generative machine learning models,
   wherein the deep generative machine learning models are trained with images of treatment adherence, the deep generative machine learning models base the modified personalized visualization on the image of treatment adherence that is previously unseen data, and the deep generative machine learning models utilize variational autoencoders that reconstruct datasets using autoencoding and decoding in view of information within the datasets.

14. The computer program product of claim 13, wherein the deep generative machine learning models include utilizing the variational autoencoders on images of the human body in different states of health or ailment based on the physical progression of ailments.

15. The computer program product of claim 13, wherein the modified personalized visualization illustrates computer enhanced items showing consequences for the nonadherence to the prescribed treatment.

16. The computer program product of claim 13, wherein the program instructions are executable to send a message to the computing device of the user, the message containing the modified personalized visualization.

17. A system comprising:
a processor, a computer readable memory, one or more computer readable storage media, and program instructions collectively stored on the one or more computer readable storage media, the program instructions executable to:
train deep generative machine learning models to learn a physical progression of ailments and healing of the ailments for a prescribed treatment;
receive an association of the prescribed treatment with a user;
receive an image of the user commencing the prescribed treatment;
generate an initial visualization by modifying the image of the user using the deep generative machine learning models to illustrate results of nonadherence to the prescribed treatment including enhanced changes to the image of the user showing consequences for nonadherence on a virtual pictorial and/or animated representation illustrating the ailment;
send a message to the computing device of the user which contains the initial visualization;
receive an image of treatment adherence by the user;
determine adherence to the prescribed treatment by extracting features from the image of treatment adherence and comparing the extracted features to known features of the prescribed treatment; and
generate a personalized visualization in response to adherence to the prescribed treatment,
wherein the deep generative machine learning models are trained with images of treatment adherence, the deep generative machine learning models base the personalized visualization on the image of treatment adherence that is previously unseen data, and the deep generative machine learning models utilize variational autoencoders that reconstruct datasets using autoencoding and decoding in view of information within the datasets.

18. The system of claim 17, wherein the personalized visualization illustrates computer enhanced items showing results of the adherence to the prescribed treatment.

19. The system of claim 17, wherein the deep generative machine learning models include utilizing the variational autoencoders on images of the human body in different states of health or ailment based on the physical progression of ailments.

20. The system of claim 17, wherein the deep generative machine learning models include generative adversarial networks on images of the human body in different states of health or ailment.

* * * * *